US005864016A

United States Patent [19]

Eibl et al.

[11] Patent Number: 5,864,016
[45] Date of Patent: Jan. 26, 1999

[54] BLOOD PRODUCT, A METHOD OF PRODUCING THE SAME AND A METHOD OF DETERMINING THE VIRUS INACTIVATION CAPACITY OF AN INACTIVATION TREATMENT

[75] Inventors: Johann Eibl; Friedrich Elsinger; Yendra Linnau, all of Vienna; Günther Wöber, Oberwaltersdorf, all of Austria

[73] Assignee: Immuno Aktiengesellschaft, Vienna, Austria

[21] Appl. No.: 281,110

[22] Filed: Jul. 28, 1994

Related U.S. Application Data

[63] Continuation of Ser. No. 900,164, Jun. 17, 1992, abandoned.

[30] Foreign Application Priority Data

Jun. 20, 1991 [AT] Austria ..................................... 1237/91

[51] Int. Cl.⁶ .............................. A61K 35/14; C12N 7/04
[52] U.S. Cl. .............................. 530/380; 435/2; 435/236; 424/530; 514/8
[58] Field of Search ........................ 435/2, 236; 424/530; 514/8; 530/380

[56] References Cited

U.S. PATENT DOCUMENTS

| | | | |
|---|---|---|---|
| 4,160,025 | 7/1979 | Eibl et al. | 424/101 |
| 4,297,344 | 10/1981 | Schwinn et al. | 424/101 |
| 4,314,997 | 2/1982 | Shanbrom | 514/8 |
| 4,315,919 | 2/1982 | Shanbrom | 424/101 |
| 4,379,085 | 4/1983 | Williams | 260/112 B |
| 4,404,187 | 9/1983 | Schwinn et al. | 424/101 |
| 4,405,603 | 9/1983 | Schwinn et al. | 424/101 |
| 4,480,029 | 10/1984 | Dolana | 435/5 |
| 4,481,189 | 11/1984 | Prince | 424/530 |
| 4,640,834 | 2/1987 | Eibl et al. | 424/94 |
| 4,814,435 | 3/1989 | Schwarz et al. | 530/383 |
| 4,904,641 | 2/1990 | Eibl et al. | 514/2 |
| 4,909,251 | 3/1990 | Seelich | 606/213 |
| 4,946,648 | 8/1990 | Dichtelmüller et al. | 435/2 |
| 5,118,794 | 6/1992 | Grangeorge et al. | 530/363 |
| 5,143,838 | 9/1992 | Kraus et al. | |
| 5,186,945 | 2/1993 | Shanbrom | 424/530 |
| 5,300,433 | 4/1994 | Hrinda et al. | 435/238 |
| 5,376,633 | 12/1994 | Lezdey et al. | 514/8 |
| 5,418,130 | 5/1995 | Platz et al. | 435/2 |

FOREIGN PATENT DOCUMENTS

| | | |
|---|---|---|
| 350 726 | 6/1979 | Austria . |
| 390 801 | 7/1990 | Austria . |
| 391808 | 12/1990 | Austria . |
| 2183/91 | 11/1991 | Austria . |
| 0015055 | 9/1980 | European Pat. Off. . |
| 0035204 | 9/1981 | European Pat. Off. . |
| 0050061 | 4/1982 | European Pat. Off. . |
| 0052827 | 6/1982 | European Pat. Off. . |
| 0053338 | 6/1982 | European Pat. Off. . |
| 0077870 | 5/1983 | European Pat. Off. . |
| 0 094 611 | 11/1983 | European Pat. Off. . |
| 0094611 | 11/1983 | European Pat. Off. . |
| 0099445 | 2/1984 | European Pat. Off. . |
| 0 117 064 | 8/1984 | European Pat. Off. . |
| 0 124 044 | 11/1984 | European Pat. Off. . |
| 0 124 506 | 11/1984 | European Pat. Off. . |
| 0124044 | 11/1984 | European Pat. Off. . |
| 0131740 | 1/1985 | European Pat. Off. . |
| 0 142 059 | 5/1985 | European Pat. Off. . |
| 0 144 709 | 6/1985 | European Pat. Off. . |
| 0159311 | 10/1985 | European Pat. Off. . |
| 0 173 242 | 3/1986 | European Pat. Off. . |
| 0177836 | 4/1986 | European Pat. Off. . |
| 0 196 761 | 10/1986 | European Pat. Off. . |
| 0 197 554 | 10/1986 | European Pat. Off. . |
| 0 278 487 | 8/1988 | European Pat. Off. . |
| 0 292 003 | 11/1988 | European Pat. Off. . |
| 0324729 | 7/1989 | European Pat. Off. . |
| 0 341 103 | 11/1989 | European Pat. Off. . |
| 0 343 275 | 11/1989 | European Pat. Off. . |
| 0341103 | 11/1989 | European Pat. Off. . |
| 0 345 246 | 12/1989 | European Pat. Off. . |
| 1 527 261 | 12/1989 | European Pat. Off. . |
| 0 378 208 | 7/1990 | European Pat. Off. . |
| 0378208 | 7/1990 | European Pat. Off. . |
| 0 439 156 | 7/1991 | European Pat. Off. . |
| 0 519 901 | 12/1992 | European Pat. Off. . |
| 0 528 701 | 2/1993 | European Pat. Off. . |
| 0 534 812 | 3/1993 | European Pat. Off. . |
| 0 541 507 | 5/1993 | European Pat. Off. . |
| 2916711 | 11/1980 | Germany . |
| 82/03871 | 11/1982 | WIPO . |
| WO 82/03871 | 11/1982 | WIPO . |
| 83/04371 | 12/1983 | WIPO . |
| 88/08710 | 11/1988 | WIPO . |
| WO 90/10712 | 9/1990 | WIPO . |
| WO 90/15613 | 12/1990 | WIPO . |

OTHER PUBLICATIONS

Brummelhuis, "Preparation of the Prothrombin Complex", *Methods of Plasma Protein Fractionation*, pp. 117–125 (1980).

Mannucci, "Outbreak of Hepatitis A Among Italian Patients with Haemophilia", *The Lancet*, vol. 339, p. 819 (Mar. 28, 1992).

Pape et al., "Standardization of an in vitro Red Blood Cell Test for Evaluating the Acute Cytotoxic Potential of Tensides", *Arzneim.–Forsch./Drug Res.* 40, pp. 498–502 (1990).

Vogelaar et al., "Contributions to the Optimal Use of Human Blood", *Vox Sanguinis*, vol. 26, (1974).

(List continued on next page.)

*Primary Examiner*—Chhaya D. Sayala
*Attorney, Agent, or Firm*—Foley and Lardner

[57] ABSTRACT

A blood product, exclusive of albumin, inactivated relative to infectious agents, the blood product conforming to a total virus reduction factor of at least 40, having a biological acitity of at least 50%, based on its activity prior to effecting inactivation of the infectious agents, the blood product being producible from conventional blood products and being virus-safe.

9 Claims, No Drawings

OTHER PUBLICATIONS

Mannucci et al., "Low Risk of Viral Infection After Administration of Vapor–Heated Factor VIII Concentrate", *Transfusion*, vol. 32, pp. 134–138 (1992).

Müller, W., "New Ion Exchangers for the Chromatography of Biopolymers", *Journal of Chromatography*, 510, pp. 133–140 (1990).

E.F. Vogelaar, "Contributions to the Optimal Use of Human Blood", 1974, vol. 26, pp. 118–127.

Hellmut Hartert, "Thrombosis and Bleeding Disorders", 1971, pp. 70–76.

T. Seelich, "Side Effects of Therapy with Clotting Factor Concentrates", 1980, pp. 199–208.

H. Suomela "Preparation and Properties of a Therapeutic Factor IX Concentrate", 1977, Vox Sanguinis, Journal of Blood Transfusion, Immunohaemotology and Immunopathology, vol. 33, pp. 37–50.

Ralph Clemens, Wie Virussicher Sind Blut Und Plasmaderivate?, Z. Allg. Med. 65, 429–433 (1989) pp. 429–433.

Commission of European Communities,"AD HOC Working Party on Biotechnology/Pharmacy" 111/8115/89–EN Final, pp. 1–15, 1989.

D.B. Rubinstein, M.D., Inability of Solvent–Detergent (S–D) Treated Factor VIII Concentrate to Inactivate Parvoviruses and Non–Lipid Enveloped Non–A, Non–B Hepatitis Virus in Factor VIII Concentrate: Advantages to Using Sterlizing 100 C Dry Heat Treatment. 1990.

A.M. Prince, The Development of Virus–Free Labile Blood Derivatives. Eui. J.Epidemiol, Jun. pp. 103–118.

Chemical Abstracts, vol. 111, Nov. 27, 1989, No. 22, 201439j.

Chemical Abstracts, vol. 114, Feb. 4, 1991, No. 5, 39082a.

Rozenberg, XII International Congress on Blood Transfusion Abstracts, Aug. 17–23, 1969, Moscow, pp. 473–475.

"The Inactivation of Viruses," Chap. 3, pp. 63–65.

Epstein, J.S., et al., "Arch. Pathol. Lab Med.," vol. 114, Mar. 1990, pp. 335–340.

Levings, R.L., "Veterinary Microbiology." vol. 9, 1984, pp. 313–328.

Morgenthaler, J.J.(ed.); Curr. Stnd. Hematol. Blood Transfus. Basel, Karger; Virus Inactivation in Plasma Products, No. 56, 1989, pp. 23–33. Heimburger, N., et al.

Rubinstein, A.I.; et al.; Vox Sang, vol. 60(1), Jan. 1991, p. 60.

Meng, Z., et al; Applied and Environmental Microbiology, vol. 53(4), Apr. 1987, pp. 727–730.

Horowitz, B., et al; Transfusion, vol. 25(6), Nov.–Dec. 1985, pp. 516–522.

Piët, M.P.J, et al.; Transfusion, vol. 30(6), Jul./Aug. 1990, pp. 591–598.

Piszkiewicz, D., et al; Thrombosis Research, vol. 55(5), Sep. 1, 1989, pp. 627–634.

Chemical Abstracts, vol. 84, No. 16, Apr. 19, 1976, US Abstract No. 111640n Dec. 25, 1975.

BLOOD PRODUCT, A METHOD OF PRODUCING THE SAME AND A METHOD OF DETERMINING THE VIRUS INACTIVATION CAPACITY OF AN INACTIVATION TREATMENT

This application is a continuation of application Ser. No. 07/900,164, filed Jun. 17, 1992, now abandoned.

BACKGROUND OF THE INVENTION

1. Field of the Invention.

The invention relates to a virus-inactivated blood product, a method of producing the same as well as a method of determining the virus-inactivating capacity of an inactivation treatment.

2. Description of Related Art

By blood products, products from human or animal blood or plasma are meant, which are intended for therapeutic, prophylactic or diagnostic applications. Such products may contain enzymes, proenzymes including coagulation factors, enzyme co-factors, enzyme inhibitors, immunoglobulins, albumin, plasminogen, fibrinogen, fibronectin or plasma.

The administration of blood products involves the risk of infection due to infectious agents possibly present in the donor plasma, such as hepatitis or AIDS viruses. Even if exclusively plasma that has been tested for its absence of these infectious agents is used, the danger that a patient might be infected cannot be excluded because of the limited sensitivity of the test methods. When producing blood products one is therefore forced to inactivate possibly present infectious agents by various methods.

There exists a great number of publications concerned with the inactivation of pathogens in blood products.

The various methods include:
- heating the blood products in aqueous solution, possibly with the addition of virucidal substances,
- heating the blood products in aqueous solution in the presence of stabilizing agents
- treating the blood products with organic solvents and/or detergents,
- heating the blood products in dry and wet states,
- combined treatment of the blood products with an organic solvent/detergent and heating the blood products in the dry state.

All these inactivation methods aim at eliminating the potential infectiousness of the preparations, while maintaining their biological activity as far as possible. However, so far this aim could only be achieved in the case of albumin preparations, by heating aqueous albumin solutions at a temperature of 60° C. for 10 h, because albumin is substantially more stable with regard to the influence of heat than all the other blood proteins.

In detail, the following publications may, e.g., be mentioned to the prior art:

DE-A- 29 16 711 describes a method of treating coagulation-factors-containing preparations in aqueous solution by applying a temperature of from 30° to 100° C., wherein an amino acid or a mono-, oligosaccharide or sugar alcohol are admixed to the solution of the coagulation factors.

EP-A2-0 053 338 describes a method of inactivating hepatitis viruses in preparations containing factors IX and X, wherein the aqueous solution of a blood preparation is heated in the presence of calcium ions and, possibly, an amino acid and/or a saccharide or a sugar alcohol at temperatures of up to 100° C.

In EP-A2-0 035 204 a method of inactivating aqueous protein solutions, which may contain factor VIII, fibronectin, globulin, fibrinogen and other proteins, is disclosed, wherein the composition is mixed with a polyol and the mixture is heated to a temperature of from 60° to 75° C.

In EP-A2-0 052 827 a method of inactivating hepatitis viruses in an aqueous solution containing factors II and VII in the presence of a chelating agent and, possibly, an amino acid and/or a saccharide or sugar alcohol is described.

In U.S. Pat. No. 4,379,085 a method for the thermal inactivation of a plasma protein, such as $C_1$-inhibitor or factor IX, in aqueous solution in the presence of potassium or ammonium citrate is disclosed.

In EP-A2-0 077 870 an inactivation method is described, in which an aqueous, factor VIII-containing solution is heated with amino acids, monosaccharides, oligosaccharides, sugar alcohols and hydrocarbon- or hydroxy-hydrocarbon-carboxylic acids having from 3 to 10 carbon atoms, to a temperature of from 50° to 80° C.

In the PCT application WO 83/04371 a method of inactivating hepatitis-viruses is disclosed, wherein a preparation containing the virus is treated at a temperature of from 4° to 40° C. with a halohydrocarbon, in particular chloroform.

EP-B1-0 015 055 discloses a method of treating a blood product, wherein the product is subjected to a microwave radiation treatment in the anhydrous condition so as to inactivate any microorganisms present.

In a treatise of the XII. International Congress on Blood Transfusion, Abstracts, "MIR" Publishers, Moscow 1969, pp. 473–475, Rosenberg et al. disclose a method of inactivating albumin-containing preparations and fibrinogen in the dry state by heating for 10 hours at 60° C.

EP-A2-0 094 611 discloses a method of treating a factor VIII-containing composition in the dry, for instance the lyophilized, state by applying a temperature of at least 60° C. for inactivating any hepatitis viruses present.

The published PCT application WO 82/03871 describes a method of treating preparations containing blood coagulation enzymes, the preparations being heated in the dry state so as to inactivate infectious viruses present; the dry state is defined to be a state with less than 5% by weight of water.

Prince et al., Eur. J. of Epidemiology, Vol. 3, No. 2, Jun. 1987, discloses that a method of dry-heating a lyophilized factor VIII concentrate at 60°°C. for 10 h results in a limited virus inactivation, but that hepatitis and also AIDS viruses can be transmitted by administering these dry-heated products. To increase the effectiveness of dry-heating, PCT application WO 88/08710 proposes a sequence of heat treatments.

Likewise, in EP-A-0 378 208, protein-containing compositons are subjected to a treatment with trialkyl phosphate in combination with a dry heating treatment.

The method of EP-B-0 159 311 suggests a treatment of blood products in the solid, wet state. A content of water, methanol or ethanol of more than 0.05 (5% by weight) and less than 0.70 (70% by weight) is adjusted and heating is effected in a closed container at a temperature in the range of from 50 ° to 121° C.

EP-B-0 050 061 discloses a method comprising the treatment of biological and pharmaceutical products with from 0.25 to 10% by weight of a non denaturating amphiphile (detergent). In EP-B-0 131 740 it is, however, shown that the treatment with a detergent alone is relatively ineffective with regard to the virus inactivation. That publication suggests a mixture of a detergent and a di- or trialkylphosphate for an effective treatment. In that instance, the concentration of the detergent was 1% by weight and that of the solvent was 0.1% by weight .

It is to be understood that the use of the percentage symbol "%" refers to a percentage by weight.

A combined treatment with an organic solvent/detergent and with heat, wherein the blood product is heated in the dry state, has also been documented in the literature (American Journal of Hematology 35, 142 (1990).

Today, virus inactivation methods are termed as effective, if after application of the method on a blood product sample admixed with a high dose of a test virus (e.g., corresponding to a maximum possible titer of approximately $10^5$ in a coagulation factor preparation), it is no longer possible to detect any viruses, the virus titer thus having been reduced to below the detection limit.

As a measure of inactivation, the so-called reduction factor is known, which is calculated after a single addition of the test virus from the decadic logarithm of the quotient of the initial and final virus titers. From the directive EC III/8115/89-EN of the Commission of the European Communities, the so-called "total reduction factor" is known. It is calculated from the sum of the reduction factors of individual subsequent inactivation measures.

In modern medicine it is necessary to administer many blood products over long periods of time—in many cases even as a permanent treatment—in large quantities, also for prophylactic reasons. This will necessarily lead to a cumulation of infectious particles and thus to a substantially increased risk of infection, even if preparations that have already been virus-inactivated are administered.

Reduction factors must be compared with the so-called "worst case situation" for a virus contamination of the entire plasma pool. For example, it is known that plasma that tests negative for HIV content may yield an HIV content of up to $10^5$ ID/ml (infectious units per milliliter) in the plasma product. See Zeitschrift für Allgemeine Medizin 65: 429–433 (1989). Thus, in the worst case, a seemingly virus-negative plasma product must be assumed to contain up to $10^5$ ID/ml. Accordingly, virus inactivation must take into account the worst case potential of virus contamination. For example, assuming that a patient is administered 100 l of a factor VIII preparation in the course of his life, a method of virus-inactivating plasma derivatives must thus permit a virus titer reduction of at least $10^{10}$ so as to avoid the infection of a patient with AIDS viruses.

SUMMARY OF THE INVENTION

The invention has as its object to provide a virus-safe blood product, exclusive of albumin, from which it can be expected that the transmission of infectious agents is excluded even if large quantitites of blood product are administered, and which nevertheless still has a high biological activity.

According to the invention, this object is achieved by a blood product, exclusive of albumin, inactivated relative to infectious agents, which blood product conforms to a total virus reduction factor of at least 40, and has a biological activity of at least 50%, based on the activity prior to carrying out the inactivation of the infectious agents, to be obtained by an inactivation treatment in which a) the blood product is treated in an aqueous solution containing at least 2%, preferably at least 5%, of a detergent, and subsequently is heated in the solid state, or b) the blood product is heated in the solid state and subsequently is treated in an aqueous solution containing at least 2%, preferably at least 5%, of a detergent.

Preferably, the invention consists in a blood product inactivated relative to infectious agents, wherein the blood product is treated in an aqueous solution containing more than 10% of a detergent and is heated in the solid state.

Another embodiment of the present invention includes a blood product, exclusive of albumin, inactivated relative to infectious agents, which blood product conforms to a total virus reduction factor of at least 40, and has a biologic activity of at least 50%, based on the activity prior to carrying out the inactivation of the infectious agents, to be obtained by an inactivation treatment comprising two or more different inactivation methods, wherein at least one method consists in a heat treatment of the blood product in solid state having a water content of from 5% by weight to 70% by weight. In this embodiment, advantageously at least one method is to be a treatment with an aqueous detergent solution.

The biological activity is determined as the enzymatic activity (e.g., of blood clotting enzymes and co-factors), as avidity (of immunoglobulins) or as antigenic activity—possibly by the use of activity or antigen markers.

DETAILED DESCRIPTION OF THE INVENTION

The blood product according to the invention may be produced from conventional blood products by carrying out the inactivation treatment for a period of time which suffices to obtain a total virus reduction factor of at least 40. This period of time may be determined experimentally in a blood product sample by repeatedly adding certain amounts of test virus during the treatment, each repetition being effected only when the virus titer has decreased to a certain value, preferably to below the detection limit. The total virus reduction factor results from the sum of the individual reduction factors. It should be noted that detection limits can be influenced by variables such as the types and concentration of the sample, the type and concentration of the detergent, and the type of contaminating virus.

Thus, if test virus is added repeatedly at chosen time intervals to a biological product during the treatment for virus inactivation, after determination of the initial and final virus titer, the decadic logarithm of the virus titer ratio may be multiplied by the number of intervals and the reduction factors may be added up to a total virus reduction factor. This calculation requires that the virus titer reduction after the final test virus addition does not exceed the previous titer reductions, as shown in the examples.

As the test virus, e.g., the AIDS virus or the Sindbis virus (as the model virus for hepatitis viruses) may be used.

The invention is based on the finding that a treatment with Tween or a detergent according to the prior art which is carried out at detergent concentrations of below 10%, does not yield a satisfactory result, if the blood product is not subjected to a further method of virus inactivation. This may be due to a protective effect of proteins on viruses against inactivating agents, such as detergents. This protective effect may, however, be eliminated by a higher concentration of Tween or detergent, respectively, without substantially impairing the biological activity of the proteins. Such a procedure makes it possible to do without the addition of further substances, such as, e.g., solvents, whose toxic effect is known.

It has proven to be advantageous if the treatment with Tween or detergent is carried out at a concentration of more than 10% and less than 25% by mass, for a period of time of between 1 min and 30 min, in particular at a pH of between 5.5 and 8, at temperatures of between 0° C. and 56° C., advantageously between 15° C. and 37° C., and optionally at an electric conductivity of from 7 to 20 mS.

A preferred method of producing inactivated blood products according to the invention consists in that the blood product is treated with hot vapor before or after the treatment with the aqueous detergent solution, wherein the blood product is adjusted to a content of water, methanol or ethanol of more than 0.05 (5% by mass) and less than 0.70 (70% by mass), preferably less than 0.40 (40% by mass) in the solid state, and is treated in a closed container at a temperature in the range of from 50° to 121° C.

The invention also relates to a method of determining the virus inactivating capacity of an inactivation treatment comprising at least one inactivation method, by determining the reduction factor by means of a test virus, which is characterized in that the test virus is repeatedly added during the at least one inactivation method, and the individual reduction factors of at least one inactivation method are optionally added up with the reduction factors of further inactivation methods to give a total virus reduction factor.

The invention will be explained in more detail by the following Examples.

EXAMPLES 1

From human plasma a coagulation-factor-VIII-containing cryoprecipitate solution was produced according to a method disclosed in AT-B 391,808. The solution was adjusted to 8% Tween 80 and 7 times admixed with a HIV-1 virus suspension at 2 min intervals. After a total incubation period of 14 min at 25° C., the virus was centrifuged and the titer was determined. The control value of the preparation without Tween addition was $10^{5.1}$. After the Tween treatment, the virus titer was below the detection limit of $10^{0.5}$ and could be termed to be 0 based on the negative tests with the reverse transcriptase. This results in a virus reduction factor of 7×5.1=35.7.

The solution freed from Tween was again admixed with HIV-1 virus suspension, lyophilized and, according to the method of EP-A-0 159 311 heated at 60° C. for 10 h at a water content of 8%. The virus titer was lowered from $10^{6.2}$ to 0.

Both inactivation steps thus resulted in a total virus reduction factor of 41.9. Thus, it could be proven that a factor VIII preparation which is subjected to the detergent and heat treatments under the conditions stated above conforms to a total virus reduction factor of 41.9 and can be viewed to be virus-safe.

The determination of the residual activity of factor VIII was effected by the aid of the thromboplastin formation test (2 step test). The residual activity of factor VIII was calculated by forming the quotient of the factor VIII activity of the heated sample and the factor VIII activity of the starting material prior to the Tween treatment and amounted to 80%.

EXAMPLE 2

A preparation containing the clotting factors II, IX and X (partial prothrombin complex, PPC) was recovered according to the method disclosed in Vox. Sang. 33, 37–50 (1977) from human plasma by adsorption on DEAE Sephadex, washing of the ionic exchanger and elution of the complex.

The PPC was admixed with HIV-1 in a solution containing 22% Tween 80 and incubated at 25° C. The virus suspension was added 15 times at 20 s intervals. The virus titer of the control without the addition of Tween was $10^{5.7}$.

After the treatment with Tween the final virus titer was below the detection limit of $10^{0.5}$. From this, a total virus reduction factor of at least 15×5.2=78 is calculated. A PPC preparation subjected to the above treatment with Tween thus corresponds to a total virus reduction factor of 78 and is to be viewed as virus-safe.

The activity of the coagulation factors was determined by way of factor IX via the addition of the sample to be tested to a factor IX deficient plasma and the determination of the activated partial thromboplastin time (1 step test) and was hardly influenced by the treatment with Tween. The ratio of the activity of the treated sample treated to the activity of factor IX in the untreated PPC was approximately 100%.

EXAMPLE 3

A PPC preparation as described in Example 2 was incubated at 25° C. with 12% dimethyl octyl amine-N-oxide in the presence of model viruses (Sindbis and vesicular stomatitis virus=VSV). The addition of virus suspension was effected 10 times at 5 min intervals. After the treatment with detergent, the virus titer was below the detection limit of $10^{1.5}$. The control values without detergent addition were $10^{6.4}$ and $10^{6.1}$, respectively. From this a total virus reduction factor of at least 10×4.9=49 and 10×4.6=46 was calculated.

The biological activity was hardly impaired by the detergent treatment and amounted to approximately 100%.

EXAMPLE 4

Plasma was fractionated according to Cohn, and the fibrinogen-containing COHN I fraction was admixed with model viruses (Sindbis or VSV, respectively). After lyophilization, the concentrate having a water content of 8% was heated according to the method of EP-A-0 159 311 for 10 hours at 60° C. and subsequently for 3 h at 80° C. The virus titer was lowered by lyophilization from $10^{5.5}$ and $10^{6}$, respectively, to $10^{4.9}$ and $10^{5.5}$, respectively, and furthermore, by the treatment at 60° C. to below the detection limit of $10^{0.5}$.

The inactivation capacity of the second treatment step at 80° C. was determined in parallel preparations: lyophilization again lowered the virus titer from $10^{5.5}$ and $10^{6.0}$ to $10^{4.9}$ and $10^{5.5}$, respectively, and further on, the treatment at 80° C. lowered it to below the detection limit.

The reduction factor is calculated from the two-time reduction by 5 or 5.5 log-steps, respectivly, minus 0.6 or 0.5 log-steps, respectively, because during the two-step treatment the fibrinogen preparation was subjected to a single lyophilization only. The reduction factors thus were 9.4 and 10.5, respectively.

Subsequently, the powder was dissolved in a medium containing 5% octyl glucoside, and at intervals of 5 min Sindbis or VSV, respectively, was added 9 times thereto. After the incubation (a total of 45 min at 25° C.) the virus titer was determined. The treatment with detergent reduced the virus titer to a value of below the detection limit of $10^{0.5}$. The control value of a preparation without detergent addition was $10^{6.9}$ and $10^{6.0}$, respectively. From this, virus reduction factors of at least 57.6 and 49.5, respectively, were calculated. Thus, the total virus reduction factors were at least 67.0 and 60.0, respectively. A fibrinogen preparation which is subjected to the heat and detergent treatments under the above indicated conditions conforms to a total virus reduction factor of at least 60.0 and is to be considered as virus-safe.

A precipitate was precipitated by adding 8% ethyl alcohol to the octyl-glucoside-containing fraction, and the biological activity of the fibrinogen was determined by means of a cross-linking test of the fibrin-α-chains (T. Seelich, H. Redl "Theoretische Grundlagen des Fibrinklebers" in K. Schimpf "Fibrinogen, Fibrin und Fibrinkleber", F. K. Schattauer Verlag, Stuttgart-New York, 199–208, 1980) and by means of thrombelastography (H. Hartert in "Thrombosis and Bleeding Disorders", (N. U. Bang et al., eds.) Georg Thieme Verlag Stuttgart, Acad. Press New York London, 70–76, 1971), coagulation factor XIII having been admixed in each case.

The biological activity of the treated fibrinogen, based on the biological activity of the COHN I fraction, was 87%, measured by the cross-linking, and 56%, measured in the thrombelastogram.

EXAMPLE 5

Selected plasma was fractionated according to Cohn. The COHN III fraction which contained anti-tetanus-toxoid gamma globulin was admixed with HIV-1 and Sindbis virus, respectively, in the presence of 15% Triton X-100 and incubated at 25° C. Virus addition was effected 30 times at one-minute intervals. After an incubation period of a total of 30 min, the virus titer was below the detection limit of $10^{2.5}$ and $10^{1.5}$, respectively. The control values of the preparation without the addition of detergent were $10^{5.7}$ and $10^{7.5}$, respectively. From this a total virus reduction factor of at least 30×3.2=96 and 30×6=180, respectively, is calculated. A gamma globulin preparation which had been subjected to the above detergent treatment corresponds to a total virus reduction factor of at least 96 and is to be viewed as virus-safe.

The biological activity was determined with an avidity test. For this, tetanus toxoid was adsorbed on a microtiter plate, covered with gelatine and washed. Subsequently, the gamma globulin to be tested was applied to the coated microtiter plate in several dilutions, and non-adsorbed immunoglobulin was washed off. The gamma globulin bound to the tetanus toxoid was determined by adsorption of an anti-human IgG peroxidase conjugate to the Fc portion of the immunoglobulin and furthermore by color reaction of the peroxidase with diaminobenzidine and $H_2O_2$ and subsequent measurement of the optical density.

The avidity of the gamma globulin for the tetanus toxoid was hardly influenced by the treatment with detergent. No significant avidity differences could be detected before and after the treatment.

EXAMPLE 6

0.95 ml of a solution containing $C_1$ esterase inhibitor (produced according to Vogelaar E F et al. (1973) Vox Sang. 26, 118–127 "Contributions to the Optimal Use of Human Blood") were admixed with 20 mg Triton X-100 and incubated at 25° C. To determine the virus inactivation capacity, VSV virus (10 µl) was repeatedly admixed at intervals of 5 min. When virus had been admixed 5 times, the virus titer was detected to be below the detection limit of $10^{0.5}$. The control value of the preparation without addition of detergent was $10^{7.5}$. From this, a virus reduction factor of at least 5×7=35 is calculated.

The $C_1$ esterase inhibitor was adsorbed on DEAE Sephadex and washed with 8.89 g/l NaCl solution until it was free of detergent. After desorption of the inhibitor with 59 g/l NaCl solution, it was dialysed against a buffer containing 1.0 g/l sodium citrate and 0.4 g/l NaCl (pH 6.8). To this solution again VSV virus was admixed before it was lyophilized. The preparation was dry-heated for 24 h at 72° C. During lyophilization and the subsequent heat treatment, the virus titer was reduced from $10^{7.2}$ to below the detection limit of $10^{0.5}$. The virus reduction factor thus was at least 6.7.

From the virus reduction factors of the detergent and thermal treatments, a total virus reduction factor of at least 41.7 is calculated. The biologic activity of the inhibitor was hardly impaired by the inactivation of the VSV viruses and was approximately 100%.

What is claimed is:

1. A virally-inactivated blood product, other than an albumin product, that has a total virus reduction factor of at least 40 and that retains at least 50% of its pre-treatment biological activity, obtainable by an inactivation treatment wherein a) a blood product is treated in an aqueous solution containing more than 10% by weight of a detergent without toxic solvents, and subsequently is heated while in a solid state to obtain the virally-inactivated blood product, or b) a blood product is heated while in a solid state and subsequently is treated in an aqueous solution containing more than 10% by weight of a detergent without toxic solve its to obtain the virally-inactivated blood product, wherein the virally-inactivated blood product obtainable by said inactivation treatment has a detergent content but is free of toxic solvents.

2. A blood product according to claim 1, wherein said solid state has a water, methanol or ethanol content of 5% by weight to 70% by weight.

3. A blood product according to claim 1, wherein the heating of said blood product is in a closed container at a temperature range of 50° C. to 121° C.

4. A method of producing a virally-inactivated blood product having a detergent content but free of toxic solvents, other than an albumin product, comprisirg the steps of, in any order:

treating a blood product in an aqueous solution containing more than 10% by weight of a detergent without toxic solvents, and heating the blood product in a solid state to obtain the virally-inactivated blood product, whereby a total virus reduction factor of at least 40 is achieved and the virally-inactivated blood product retains at least 50% of its pre-treatment biological activity.

5. A method according to claim 4, wherein said solid state has a water, methanol or ethanol content of from 5% by weight to 70% by weight.

6. A method according to claim 4, wherein the heating of said blood product is in a closed container at a temperature range of 50° C. to 121° C.

7. A method of inactivating viruses in a blood sample to produce a non-albumin, virally-inactivated blood product having a detergent content but free of toxic solvents, comprising the steps of, in any order:

treating said blood sample in an aqueous solution with a detergent present in an amount of at least 2% by weight without toxic solvents; and heating said blood sample in a solid state, wherein said blood sample has a water, methanol or ethanol content of 5% to 70% by weight and is not in solution, whereby after said treating and heating steps said virally-inactivated blood product retains at least 50% of its pre-treatment biological activity and wherein said virally-inactivated blood product has a virus reduction factor of at least 40.

8. A method according to claim 7, wherein said blood product is a coagulation factor.

9. A method according to claim 7, wherein said blood product is an immunoglobulin.

* * * * *